(12) United States Patent
Hon

(10) Patent No.: US 8,490,628 B2
(45) Date of Patent: Jul. 23, 2013

(54) ELECTRONIC ATOMIZATION CIGARETTE

(75) Inventor: Lik Hon, North Point (HK)

(73) Assignee: Ruyan Investment (Holdings) Limited;, Tortola (VG)

( * ) Notice: Subject to any disclaimer, the term of this patent is extended or adjusted under 35 U.S.C. 154(b) by 0 days.

(21) Appl. No.: 13/560,789

(22) Filed: Jul. 27, 2012

(65) Prior Publication Data

US 2012/0285476 A1 Nov. 15, 2012

Related U.S. Application Data

(63) Continuation of application No. 12/944,123, filed on Nov. 11, 2010, now Pat. No. 8,393,331, which is a continuation of application No. 10/587,707, filed as application No. PCT/CN2005/000337 on Mar. 18, 2005, now Pat. No. 7,832,410.

(30) Foreign Application Priority Data

Apr. 14, 2004 (CN) .............................. 20040031182

(51) Int. Cl.
*A24F 1/32* (2006.01)

(52) U.S. Cl.
USPC ........... 131/194; 131/271; 131/273; 131/270; 128/202.21

(58) Field of Classification Search
USPC .............. 131/329, 194, 270–273; 128/202.21
See application file for complete search history.

(56) References Cited

U.S. PATENT DOCUMENTS

| | | | |
|---|---|---|---|
| 1,775,947 A | 5/1927 | Robinson |
| 2,057,353 A | 10/1936 | Whittemore |
| 2,631,219 A | 3/1953 | Suchy |
| 3,200,819 A | 8/1965 | Gilbert |
| 3,551,643 A | 12/1970 | Pricenski |
| 4,171,000 A | 10/1979 | Uhle |
| 4,207,457 A | 6/1980 | Haglund |
| 4,641,053 A | 2/1987 | Takeda |
| 4,735,217 A | 4/1988 | Gerth |
| 4,756,318 A | 7/1988 | Clearman |
| 4,771,796 A | 9/1988 | Myer |
| 4,819,665 A | 4/1989 | Roberts |
| 4,848,374 A | 7/1989 | Chard |
| 4,945,929 A | 8/1990 | Egilmex |

(Continued)

FOREIGN PATENT DOCUMENTS

| | | |
|---|---|---|
| CN | 89207339X | 5/1989 |
| CN | 2047485 U | 11/1989 |

(Continued)

OTHER PUBLICATIONS

FIN Branding Group, LLC, Third Party Response to Amendment including Submission of Prior Arts and Misc. Statement Per 37 CFR 1.948 and Oljaca 6601776 in Reexamination of U.S. Patent No. 8,156,944, Sep. 13, 2012.

(Continued)

*Primary Examiner* — Richard Crispino
*Assistant Examiner* — Dionne Walls Mayes
(74) *Attorney, Agent, or Firm* — Kenneth H. Ohriner; Perkins Coie LLP

(57) ABSTRACT

An electronic cigarette includes a shell and a mouthpiece. The external wall of the shell has an air inlet. An atomizer and a liquid-supply are in contact with each other. The air inlet, atomizer, an aerosol passage, and a mouthpiece are sequentially interconnected.

8 Claims, 5 Drawing Sheets

U.S. PATENT DOCUMENTS

| | | | |
|---|---|---|---|
| 4,945,931 | A | 8/1990 | Gori |
| 4,947,875 | A | 8/1990 | Brooks |
| 5,042,470 | A | 8/1991 | Kanesaka |
| 5,060,671 | A | 10/1991 | Counts et al. |
| 5,080,114 | A | 1/1992 | Rudolph et al. |
| 5,095,921 | A | 3/1992 | Losee |
| 5,144,962 | A | 9/1992 | Counts |
| 5,159,940 | A | 11/1992 | Hayward et al. |
| 5,190,060 | A | 3/1993 | Gerding |
| 5,224,498 | A | 7/1993 | Deevi |
| 5,249,586 | A | 10/1993 | Morgan et al. |
| 5,261,424 | A | 11/1993 | Sprinkel, Jr. |
| 5,285,798 | A | 2/1994 | Banerjee |
| 5,322,075 | A | 6/1994 | Deevi |
| 5,388,594 | A | 2/1995 | Counts |
| 5,438,978 | A | 8/1995 | Hardester |
| 5,497,791 | A | 3/1996 | Bowen et al. |
| 5,505,214 | A | 4/1996 | Collins |
| 5,591,368 | A | 1/1997 | Fleischhauer et al. |
| 5,666,977 | A | 9/1997 | Higgins |
| 5,666,978 | A | 9/1997 | Counts |
| 5,730,158 | A | 3/1998 | Collins |
| 5,743,251 | A | 4/1998 | Howell |
| 5,799,663 | A | 9/1998 | Gross |
| 5,819,756 | A | 10/1998 | Mielordt |
| 5,878,752 | A | 3/1999 | Adams et al. |
| 5,894,841 | A | 4/1999 | Voges |
| 6,040,560 | A | 3/2000 | Fleischhauer |
| 6,041,789 | A | 3/2000 | Bankert |
| 6,095,153 | A | 8/2000 | Kessler |
| 6,164,287 | A | 12/2000 | White |
| 6,178,969 | B1 | 1/2001 | St. Charles |
| 6,196,218 | B1 | 3/2001 | Voges |
| 6,354,293 | B1 | 3/2002 | Madison |
| 6,357,671 | B1 | 3/2002 | Cewers |
| 6,443,146 | B1 | 9/2002 | Voges |
| 6,532,965 | B1 | 3/2003 | Abhulimen |
| 6,601,776 | B1 | 8/2003 | Oljaca et al. |
| 6,715,494 | B1 | 4/2004 | McCoy |
| 6,772,756 | B2 | 8/2004 | Shayan |
| 6,803,545 | B2 | 10/2004 | Blake |
| 6,810,883 | B2 | 11/2004 | Felter |
| 6,854,461 | B2 | 2/2005 | Nichols |
| 6,854,470 | B1 | 2/2005 | Pu |
| 7,100,618 | B2 | 9/2006 | Dominguez |
| 7,131,599 | B2 | 11/2006 | Katase |
| 7,726,320 | B2 | 6/2010 | Robinson |
| 7,832,410 | B2 | 11/2010 | Hon |
| 7,845,359 | B2 | 12/2010 | Montaser |
| 7,997,280 | B2 | 8/2011 | Rosenthal |
| 2003/0108342 | A1 | 6/2003 | Sherwood et al. |
| 2004/0182403 | A1 | 9/2004 | Andersson et al. |
| 2004/0261802 | A1 | 12/2004 | Griffin et al. |
| 2005/0016550 | A1 | 1/2005 | Katase |
| 2005/0236006 | A1 | 10/2005 | Cowan |
| 2006/0196518 | A1 | 9/2006 | Hon |
| 2008/0276947 | A1 | 11/2008 | Martzel |
| 2009/0095311 | A1 | 4/2009 | Han |
| 2009/0126745 | A1 | 5/2009 | Hon |
| 2009/0151717 | A1 | 6/2009 | Bowen |
| 2009/0188490 | A1 | 7/2009 | Han |
| 2009/0230117 | A1 | 9/2009 | Fernando |
| 2009/0260642 | A1 | 10/2009 | Monsees |
| 2009/0272379 | A1 | 11/2009 | Thorens |
| 2010/0031968 | A1 | 2/2010 | Sheikh |
| 2010/0126505 | A1 | 5/2010 | Rinker |
| 2010/0181387 | A1 | 7/2010 | Zaffaroni |
| 2010/0200008 | A1 | 8/2010 | Teieb |
| 2010/0242974 | A1 | 9/2010 | Pan |
| 2010/0307518 | A1 | 12/2010 | Wang |
| 2011/0005535 | A1 | 1/2011 | Xiu |
| 2011/0036346 | A1 | 2/2011 | Cohen |
| 2012/0111347 | A1 | 5/2012 | Hon |

FOREIGN PATENT DOCUMENTS

| | | | |
|---|---|---|---|
| CN | 1135860 | | 11/1996 |
| CN | 97216131 | | 5/1997 |
| CN | 2293957 | Y | 10/1998 |
| CN | 1252961 | | 5/2000 |
| CN | 200410048792.6 | | 6/2004 |
| CN | 1575673 | | 2/2005 |
| CN | 200520089947 | | 3/2005 |
| CN | 2777995 | Y | 5/2006 |
| CN | 1284493 | C | 11/2006 |
| CN | 20062135072 | U | 12/2006 |
| CN | 20071121524 | | 9/2007 |
| CN | 200997909 | Y | 1/2008 |
| CN | 101116542 | A | 2/2008 |
| CN | 101176805 | A | 5/2008 |
| DE | 10051792 | | 5/2002 |
| EP | 0057243 | | 8/1982 |
| EP | 0230420 | | 8/1987 |
| EP | 0295122 | A1 | 12/1988 |
| EP | 0342538 | | 11/1989 |
| EP | 0358002 | | 3/1990 |
| EP | 0295122 | B1 | 1/1992 |
| EP | 0545186 | | 6/1993 |
| EP | 0703735 | | 4/1996 |
| EP | 0824927 | | 2/1998 |
| EP | 0845220 | | 6/1998 |
| EP | 0893071 | | 1/1999 |
| EP | 0951219 | | 11/2002 |
| GB | 1528391 | A | 10/1978 |
| JP | 64000498 | | 1/1989 |
| JP | 06114105 | | 4/1994 |
| JP | 07506999 | | 8/1995 |
| JP | 09075058 | | 3/1997 |
| UA | UA47514 | | 12/1997 |
| WO | WO9409842 | | 5/1994 |
| WO | WO9421317 | | 9/1994 |
| WO | WO9740876 | | 11/1997 |
| WO | WO9748293 | | 12/1997 |
| WO | WO9817130 | | 4/1998 |
| WO | WO0049901 | | 8/2000 |
| WO | WO0105459 | | 1/2001 |
| WO | WO03034847 | | 1/2003 |
| WO | WO03022364 | | 3/2003 |
| WO | WO03055486 | | 7/2003 |
| WO | WO03101454 | | 12/2003 |
| WO | WO2004001407 | | 12/2003 |
| WO | WO2004023222 | | 3/2004 |
| WO | WO2004080216 | | 9/2004 |
| WO | WO2006082571 | | 8/2006 |
| WO | WO2007078273 | | 7/2007 |
| WO | WO2008077271 | | 7/2008 |
| WO | WO2008130813 | | 10/2008 |
| WO | WO2009118085 | | 10/2009 |
| WO | WO2009135729 | | 11/2009 |
| WO | WO2010052323 | | 5/2010 |
| WO | 2010145468 | | 12/2010 |
| WO | WO2010145805 | | 12/2010 |
| WO | WO2011010334 | | 1/2011 |
| WO | WO2011022431 | | 2/2011 |

OTHER PUBLICATIONS

Australian Patent Office, Examination Report for SG 200505930-8, dated May 4, 2006.

Australian Patent Office; Exam Report for AU2004234199, dated Aug. 14, 2009.

Australian Patent Office; Search and Examination Report for SG200604498-6, dated Apr. 16, 2008.

CN Creative ; Intellicig USA, *Ruyan v. Smoking Everywhere et al.* CV11-6268 Invalidity Contentions, Apr. 12, 2012.

Cyphert, GIL DBA NU1S, *Ruyan v. Smoking Everywhere et al.* CV11-0367 Invalidity Contentions, Apr. 11, 2012.

European Patent Office, Extended European Search Report for EP07721148, Dec. 6, 2010.

European Patent Office, Extended European Search Report for EP11001479, Jul. 4, 2011.

European Patent Office, Supplemental Extended European Search Report for EP04718242, dated Jul. 27, 2007.

European Patent Office, Supplemental Extended European Search Report for EP05729107, dated Jul. 31, 2007.

European Patent Office, Supplemental Partial Extended European Search Report for EP05729107, dated May 22, 2007.

European Patent Office, Supplemental Partial Extended European Search Report for EP04718242, dated May 22, 2007.
FIN Branding Group, LLC, Request for Inter Partes Reexamination of U.S. Patent No. 8,156,944, filed Sep. 13, 2012.
Introduction to selecting and using electronic components, ISBN7-111-13752-3.
IP Australia, Patent Examination Report No. 1 for AU2007250367, Jul. 30, 2012.
IP Australia, Patent Examination Report No. 1 for AU2007250368, Aug. 9, 2012.
Japanese Patent Office, Office Action and English Translation for JP2006504199, dated Oct. 30, 2009.
Korean Intellectual Property Office, Notice of Preliminary Rejection for KR1020057009767, dated Jul. 27, 2009.
Macau Patent Office, Official Communication for MOI121, dated Apr. 17, 2009.
Malaysian Patent Office, Examiner's Report for MY PI 20041407, dated Sep. 28, 2007.
Manual for Electric Engineers, 2nd Ed, Mar. 2000.
Manual for Mechanical Designers, 4th Ed, Jan. 2002.
Materials Manual-Nonmetal, Jul. 1, 1985.
Sottera, Inc., *Ruyan v. Smoking Everywhere et al.* CV11-0367 Invalidity Contentions, Apr. 12, 2012.
Sottera, Inc., *Ruyan v. Smoking Everywhere et al.* CV11-0367 Invalidity Contentions, Exhibit 7 (Claim 20 Claim Chart), Apr. 12, 2012.
Sottera, Inc., *Ruyan v. Smoking Everywhere et al.* CV11-0367 Invalidity Contentions, Exhibit 8 (Claim 24 Claim Chart), Apr. 12, 2012.
State Intellectual Property Office, P.R. China, English Translation of Written Opinion for PCT/CN07/001575, Jul. 20, 2007.
State Intellectual Property Office, P.R. China, English translation of Written Opinion for PCT/CN07/001576, Aug. 3, 2007.
State Intellectual Property Office, P.R. China, International Search Report for PCT/CN07/001576, Aug. 16, 2007.
State Intellectual Property Office, P.R. China, International Search Report for PCT/CN07/001575, Aug. 16, 2007.
State Intellectual Property Office, P.R. China, International Search Report for PCT/CN04/000182, dated Jun. 10, 2004.
State Intellectual Property Office, P.R. China, International Search Report for PCT/CN05/000337, Jul. 14, 2005.
State Intellectual Property Office, P.R. China, International Search Report for PCT/CN10/000125, Apr. 1, 2010.
State Intellectual Property Office, P.R. China, International Search Report for PCT/CN10/073613, Aug. 26, 2010.
State Intellectual Property Office, P.R. China, Search Report for CN ZL 200620090805.0, Nov. 18, 2008.
Taiwan Patent Office, Official Letter for TW093111573, dated Apr. 24, 2009.
TechPowerUp "What is a MOSFET, what does it look like and how does it work?" May 24, 2004.
Ukraine Patent Office, Examination Report for UA200511258, dated Feb. 4, 2009.
United States Patent and Trademark Office, Office Action in Inter Partes Reexamination of U.S. Patent No. 8,156,944, mailed Nov. 27, 2012.
Machine translation Chinese Patent Application 200420031182 which corresponds to the priority document of WO2005/099494 (Hon '494) Oct. 27, 2005.
Machine translation of Chinese Patent Application 03111582.9 which corresponds to the priority document of WO2004/095955 (Hon '955) Nov. 11, 2004.

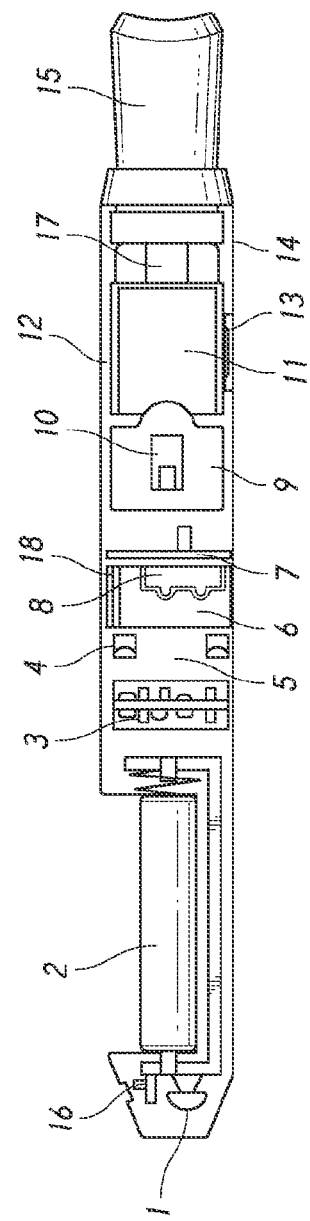
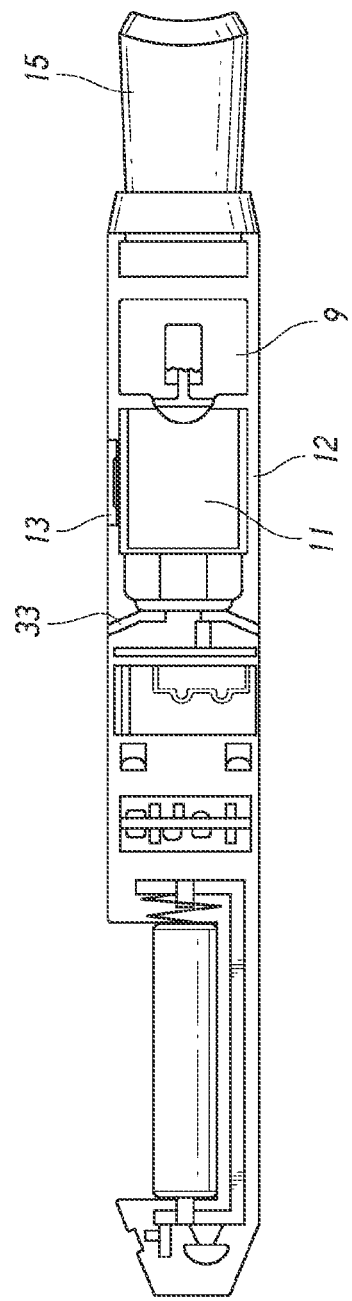
FIG. 1
FIG. 2

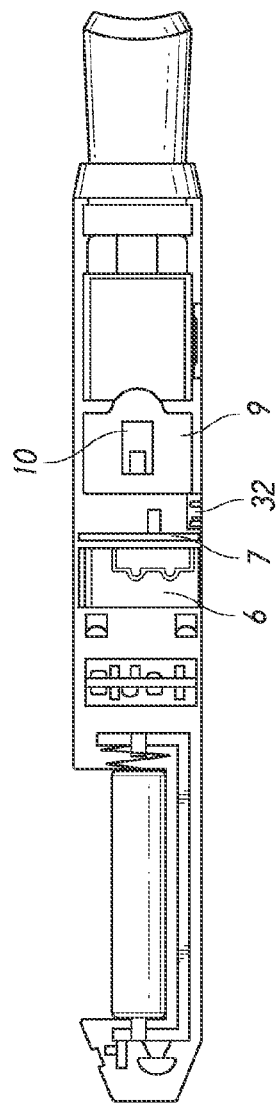
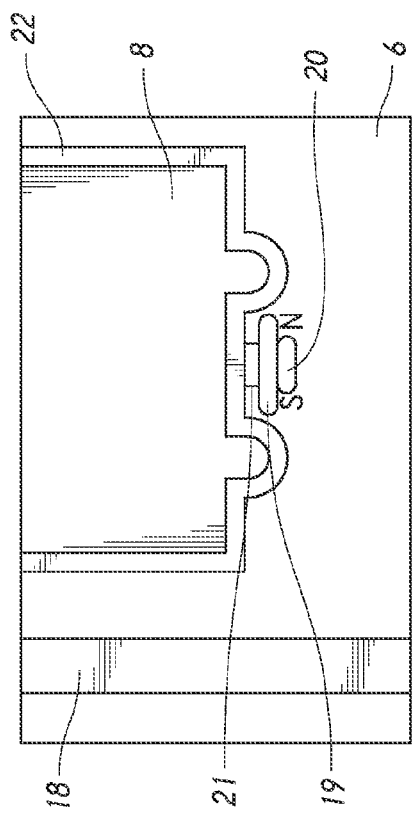
FIG. 3
FIG. 4

ELECTRONIC ATOMIZATION CIGARETTE

CROSS REFERENCE TO RELATED APPLICATIONS

This application is a continuation of U.S. patent application Ser. No. 12/944,123, filed Nov. 11, 2010 and now pending, which is a continuation of U.S. patent application Ser. No. 10/587,707, filed Mar. 9, 2007, now U.S. Pat. No. 7,832, 410B2 which claims the benefit of International PCT Application No. PCT/CN05/00337, filed Mar. 18, 2005, which claims the benefit of Chinese Patent Application No. 200400311820, filed Apr. 14, 2004, all of which are incorporated herein by reference in their entirety.

TECHNICAL FIELD

The present invention relates to an electronic cigarette, in particular to an electronic atomization cigarette that contains only nicotine without tar.

BACKGROUND ART

Although it is commonly known that "smoking is harmful to your health", the number of smokers worldwide is up to 1 billion, and the number is increasing every year. According to the statistical data from the World Health Organization, about 4.9 million people die of smoking diseases each year. Although smoking may cause serious respiratory diseases and cancer, it remains extremely difficult for smokers to quit smoking completely.

The active ingredient in a cigarette is nicotine. During smoking, nicotine, along with tar aerosol droplets, enter the smoker's alveolus and are rapidly absorbed. The nicotine then affects the receptors of the smoker's central nervous system.

Nicotine is a kind of alkaloid with low molecular weight. A small dose of nicotine is essentially harmless to human body and its half-life in blood is quite short. The major harmful substance in tobacco is tar. Tar in tobacco is composed of thousands of ingredients. Several of these are cancerogenic.

Some cigarette substitutes that contain only nicotine without tar have been proposed. Many of them, such as "nicotine patch", "nicotine mouthwash", "nicotine chewing gum", "nicotine drink" etc., are made of pure nicotine. Although these cigarette substitutes are free from tar, their major disadvantage is that an effective peak concentration can not be reached in the blood of a smoker due to slow absorption of nicotine In addition, these cigarette substitutes can not satisfy habitual smoking actions of a smoker, for example, inhaling action, and thus are not likely to be widely accepted as effective substitutes for smoking.

THE SUMMARY OF THE INVENTION

An electronic atomization cigarette that functions as substitutes for quitting smoking and cigarette substitutes includes a shell; a mouthpiece; an air inlet provided in the external wall of the shell; an electronic circuit board, a normal pressure cavity, a sensor, a vapor-liquid separator, an atomizer, and a liquid-supply arranged sequentially within the shell. A stream passage is provided on one side of the sensor. A negative pressure cavity provided in the sensor. An atomization cavity is arranged in the atomizer. The electronic circuit board comprises an electronic switching circuit and a high frequency generator. The liquid-supply is in contact with the atomizer.

With slight modification of the solution storage container, the device and connecting structures of the present invention can be filled with conventional drug for pulmonary administration apparatus.

DESCRIPTION OF THE DRAWINGS

FIG. 1 is a schematic diagram of an overall structure;
FIG. 2 is a schematic diagram of another overall structure;
FIG. 3 is a schematic diagram of a overall structure with a display screen;
FIG. 4 is a structural diagram of a sensor.

DETAILED DESCRIPTION OF THE INVENTION

Figure 5:
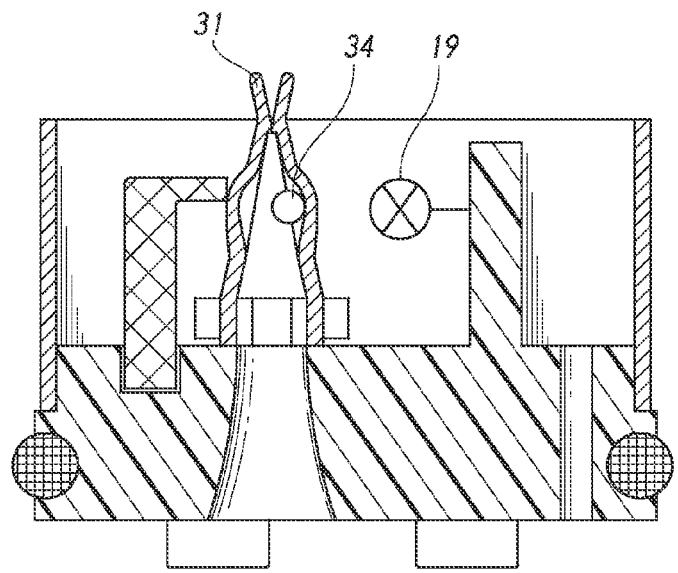
FIG. 5 is a structural diagram of a sensor with a silicon gel check valve.

The present invention is further described below with reference to the accompanying drawings.
Embodiment 1

As shown in FIG. 1, an air inlet 4 is provided on the external wall of the shell 14. A LED 1, a cell 2, an electronic circuit board 3, a normal pressure cavity 5, a sensor 6, a vapor-liquid separator 7, an atomizer 9, a liquid-supplying bottle 11 and a mouthpiece 15 are sequentially provided within the shell 14. The electronic circuit board 3 comprises an electronic switching circuit and a high frequency generator.

As shown in FIG. 4, a negative pressure cavity 8 is provided in the sensor 6 and is separated from the sensor 6 by a film 22 A first magnetic steel 20, a second magnetic steel 21 and a Reed switch 19 arranged between them is also provided within the sensor 6. The second magnetic steel 21 is attached to the film 22. The atomizer 9 is in contact with the liquid-supplying bottle 11 via the bulge 36, and the atomization cavity 10 is provided in the atomizer 9.

Figure 6:
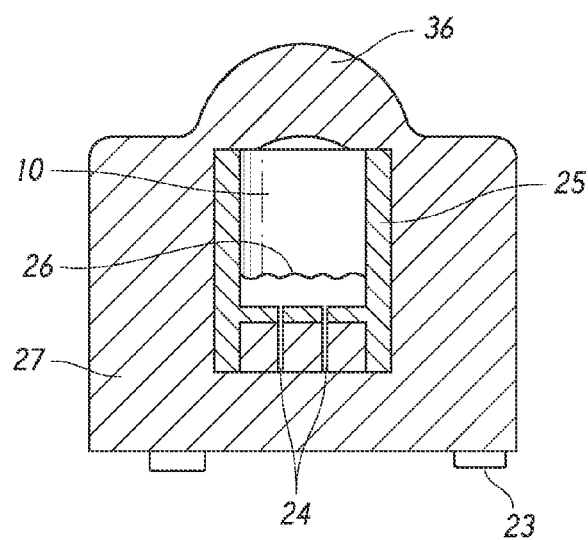
FIG. 6 is a structural diagram of an atomizer.
Figure 7:
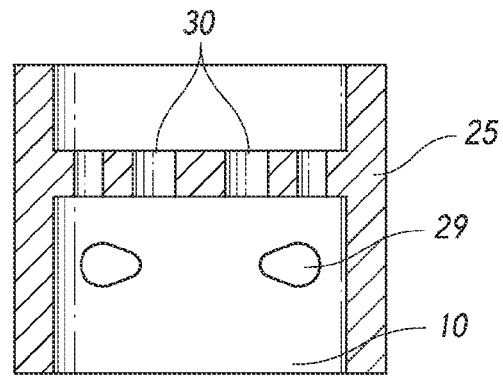
FIG. 7 is a structural diagram of the ceramic member in an atomizer.

As shown in FIGS. 6 and 7, the overflow hole 29 is provided on the wall 25 of the atomization cavity 10. A heating element 26, which can be made of platinum wire, nickel chromium alloy or iron chromium aluminum alloy wire with rare earth element, is provided within the cavity, and can also be made into a sheet form with conductive ceramics or PTC ceramics. An ejection hole is provided on the side opposite to the heating element 26. The ejection hole can be determined to select either the long stream ejection hole 24 or the short stream ejection hole 30, depending on the material used for the atomization cavity wall 25. The long stream ejection hole 24 can employ slot structure of 0.1 mm–1.3 mm or circular hole structure with a single and multiple holes. The short stream ejection hole 30 has the diameter of about 0.3 mm–1.3 mm.

Figure 9:
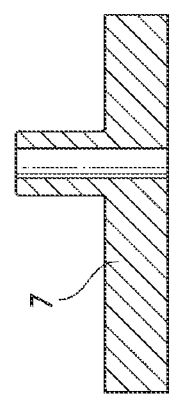
FIG. 9 is a structural diagram of a vapor-liquid separator.

The atomization cavity wall 25 is surrounded with the porous body 27, which can be made of foam nickel, stainless steel fiber felt, high molecule polymer foam and foam ceramic. A first piezoelectric element 23 is also provided on the atomizer 9. The atomization cavity wall 25 can be made of aluminum oxide or ceramic. As shown in FIG. 9, a through hole is provided on the vapor-liquid separator 7, and can be made of plastic or silicon rubber. As shown in FIG. 2, a retaining ring 13 for locking the liquid-supplying bottle 11 is provided between one side of the liquid-supplying bottle 11 and the shell 14. An aerosol passage 12 is provided on the other side of the liquid-supplying bottle.

Figure 11:
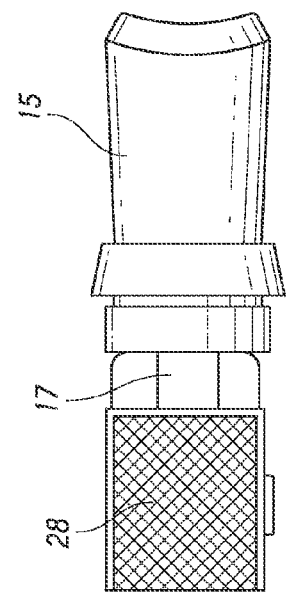
FIG. 11 is a structural diagram of the connection of a liquid-supplying bottle and a mouthpiece.

As shown in FIG. 11, the solution storage porous body 28 is provided in the liquid-supplying bottle, and can be filled with polypropylene fiber, terylene fiber or nylon fiber, or be filled with plastic shaped by foaming, such as polyamine resin foam column or polypropylene foam column. Alternatively, it may be made of a column formed by molding polyvinyl chloride, polypropylene, polycarbonate into a stack of laminated layers. The air inlet 4, normal pressure cavity 5, vapor-liquid separator 7, atomizer 9, aerosol passage 12, gas vent 17, mouthpiece 15 are sequentially interconnected.

Figure 12:
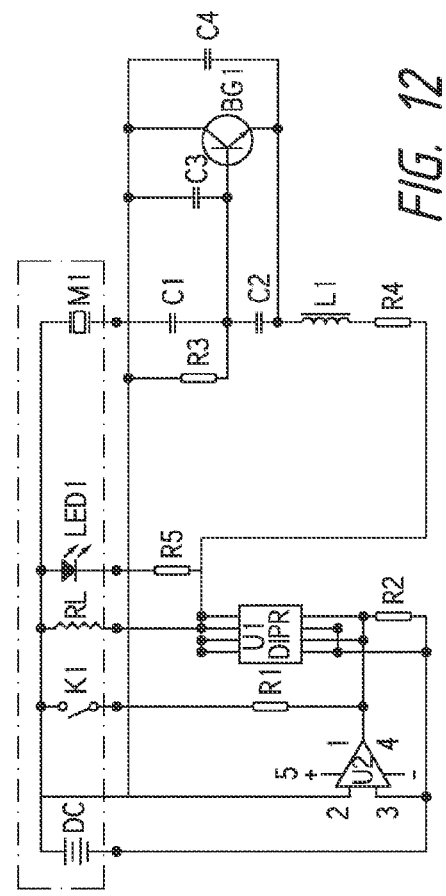
FIG. 12 is a functional diagram of a circuit.

As shown in the functional diagram of the circuit in FIG. 12, K1 refers to the Reed switch 19, RL refers to the heating element 26, LED1 refers to the Light Emitting Diode 1, U2 refers to the low voltage detecting element used for the over-discharging protection of the lithium cell, M1 refers to the first piezoelectric element 23, and C1, C2, R3, L1, C3, BG, M1 collectively constitute a Colpitts oscillator. The operating principle of the circuit is as follows: when K1 is closed, U1, i.e., the field effect power transistor, is turned on, RL starts, and the Colpitts oscillator starts oscillating, M1 will provide the high frequency mechanical oscillatory wave to the atomizer 9.

When a smoker smokes, the mouthpiece 15 is under negative pressure. The air pressure difference or high speed stream between the normal pressure cavity 5 and the negative pressure cavity 8 causes the sensor 6 to output an actuating signal, the electronic circuit board 3 connected therewith goes into operation. Now the ripple film 22 in the sensor 6 is deformed to take the second magnetic steel 21 away from the Reed switch 19. The Reed switch 19 is then closed (i.e., K1 is closed) under the effect of the excessive magnetic line of force from the first magnetic steel 20, starting the field effect power transistor electronic switch (i.e., U1 is opened). The high frequency oscillator may uses the Colpitts oscillator with the frequency of 550 KHz-8 MHz. The automatic fine-adjusting element in the circuit resonates with the first piezoelectric element 23. The LED 1 can be lit under the supply of the rechargeable battery 2.

Air enters the normal pressure cavity 5 through the air inlet 4, passes through the air passage 18 of the sensor and then the through hole in the vapor-liquid separator 7, and flows into the atomization cavity 10 in the atomizer 9. The high speed stream passing through the ejection hole drives the nicotine solution in the porous body 27 to eject into the atomization cavity 10 in the form of droplets, where the nicotine solution is subjected to the ultrasonic atomization by the first piezoelectric element 23 and is further atomized by the heating element 26.

After the atomization the droplets with large diameters stick to the wall under the action of eddy flow and are reabsorbed by the porous body 27 via the overflow hole 29. Droplets with small diameters float in stream and form aerosols, which are sucked out via the aerosol passage 12, gas vent 17 and mouthpiece 15. The solution storage porous body 28 in the liquid-supplying bottle 11 is in contact with the bulge 36 on the atomizer 9, thereby achieving the capillary infiltration liquid-supplying.

The mouthpiece 15 is threaded. When the nicotine solution in the liquid-supplying bottle 11 is used up, users can screw the mouthpiece 15 out to take the liquid-supplying bottle 11 out, refill the liquid-supplying bottle 11 with the nicotine solution, put the liquid-supplying bottle 11 into the shell 14 again, and then screw the mouthpiece 15.

The Reed switch 19, the first magnetic steel 20, the second magnetic steel 21, the ripple film 22 can be replaced by a semiconductor strain gauge with sealed film, which is mounted in the place of the sensor ripple film.

Figure 8:
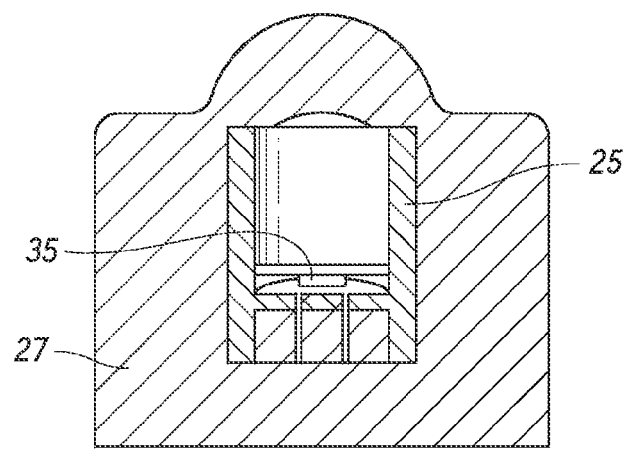
FIG. 8 is a structural diagram of another atomizer.

To simplify the design, the first piezoelectric element 23 on the atomizer 9 can be omitted, and the atomization of the nicotine solution will be made only by the heating element 26. The size of such an atomizer can be made smaller, and the structure of the connection of the whole electronic atomization cigarette is the same as the embodiment 1. In addition, as shown FIG. 8, the first piezoelectric element 23 and the heating element 26 in the atomizer 9 can be omitted, an additional second piezoelectric element 35 in the form of platen with a single layer or multiple laminated layers can be arranged in the atomization cavity, and the stream passing through the ejection hole vibrates the focus at the center of the second piezoelectric element 35 to achieve the effect of strong ultrasonic atomization.

Figure 10:
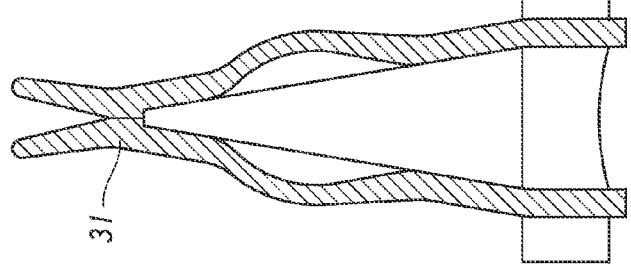
FIG. 10 is a structural diagram of another vapor-liquid separator.

As shown in FIG. 10, a silicon gel check valve 31 may cover the outside of the through hole on the vapor-liquid separator 7. During smoking, a stream reaches the through hole, as the air pressure in the through hole increases, the silicon gel check valve 31 is opened and the stream passes; otherwise, the silicon gel check valve 31 is closed.

As shown in FIG. 5, the sensor 6 may also be designed into a structure with the silicon gel check valve 31. During smoking, the stream comes into the silicon gel check valve 31, the air pressure increases and the air expands, the third magnetic steel 34 in the valve approaches the Reed switch 19 gradually until the Reed switch is closed and the circuit is turned on, and the air outlet of the silicon gel check valve 31 is opened with the increment of the air pressure difference. The Reed switch 19 can also be made of Hall device or magneto diode or magneto triode instead.

Embodiment 2

As shown in FIG. 2, to improve the liquid-supplying state, the liquid-supplying bottle 11 is arranged between the vapor-liquid separator 7 and the atomizer 9. A spring piece 33 for pressing the liquid-supplying bottle 11 on the atomizer 9 is provided on one end of the liquid-supplying bottle 11. Other components and their functions are the same as those in the embodiment 1.

On the inner wall of the shell 14 of the electronic atomization cigarette described in the embodiment 1 and 2, a digital display screen 32 for showing the smoking times per day and the cell capacity can be also provided. The sensor 6 uses a linear signal output, which is proportional to the suction force (i.e., the stronger one sucks, the longer the time of operation is), the atomizer 9 operates in the linear mode, thereby simulating a cigarette that looks like a normal cigarette.

Within the shell 14, the microswitch 16 is connected to the sensor 6 in parallel and used for manually cleaning. When users do not smoke, they press the microswitch 16 to start the sensor 6 connected therewith in parallel, or clean the residue or other impurity substance within the shell 14.

The nicotine solution for atomization contains 0.4-3.5% nicotine, 0.05-2% cigarette essence, 0.1-3.1% organic acid, 0.1-0.5% anti-oxidation agent, and the rest is 1,2-propylene glycol.

The invention claimed is:
1. An electronic cigarette, comprising:
a housing having a longitudinal axis, an inlet and an outlet;
a liquid supply in the housing;
an air flow channel in the housing connecting the inlet to the outlet; and an atomizer assembly in the housing between the inlet and the outlet, including:
- a porous body projecting into the liquid supply; and
- a heating wire in the atomizer having a central axis oriented substantially perpendicular to the longitudinal axis of the housing.

2. The electronic cigarette of claim 1 further including a battery, a sensor and an electronic circuit board within the housing, with the circuit board electrically connected to the battery, the sensor and the heating wire.

3. The electronic cigarette of claim 1 further including an atomization cavity within the atomizer.

4. The electronic cigarette of claim 1 with the outlet within a mouthpiece that is screwed onto the housing.

5. The electronic cigarette of claim 1 with the liquid supply comprising a fiber material.

6. The electronic cigarette of claim 1 with the porous body of atomizer projecting into the liquid supply comprising a porous bulge section.

7. An electronic cigarette, comprising:
- a housing having an inlet and an outlet;
- a liquid supply in the housing;
- an air flow channel through the housing connecting the inlet to the outlet, with part of the air flow channel extending alongside of the liquid supply; and
- an atomizer in the housing between the inlet and the outlet, the atomizer including:
- a porous body extending into the liquid supply;
- a heating wire in the atomizer having a central axis oriented substantially perpendicular to a longitudinal axis of the housing; and
- a battery, a sensor and an electronic circuit board within the housing, with the circuit board electrically connected to the battery, the sensor and the heating wire.

8. An electronic cigarette, comprising:
- a housing having an inlet and an outlet ;
- a liquid supply, a battery, and an electronic circuit board in the housing;
- an air flow channel in the housing between the inlet and the outlet; and
- an atomizer in the housing including: a porous body extending into the liquid supply; a heating wire having a central axis generally perpendicular to a longitudinal axis of the housing; and with the circuit board electrically connected to the battery and the heating wire.

* * * * *